(12) United States Patent
Hammond, Jr. et al.

(10) Patent No.: US 12,194,246 B2
(45) Date of Patent: Jan. 14, 2025

(54) COIL CATHETER METHOD OF MANUFACTURE

(71) Applicant: Blue Halo BioMedical LLC, Winter Park, FL (US)

(72) Inventors: Gaines Hammond, Jr., Greenville, SC (US); Byron Hodge, Jr., Lakeland, FL (US); Gary J. Mishkin, Potomac, MD (US); Anthony R. Ruben, Winter Park, FL (US)

(73) Assignee: Blue Halo BioMedical LLC, Winter Park, FL (US)

( * ) Notice: Subject to any disclaimer, the term of this patent is extended or adjusted under 35 U.S.C. 154(b) by 194 days.

(21) Appl. No.: 17/863,795

(22) Filed: Jul. 13, 2022

(65) Prior Publication Data

US 2022/0339401 A1    Oct. 27, 2022

Related U.S. Application Data

(63) Continuation of application No. 17/850,389, filed on Jun. 27, 2022, which is a continuation-in-part of
(Continued)

(51) Int. Cl.
*B29C 33/02* (2006.01)
*A61F 2/04* (2013.01)
(Continued)

(52) U.S. Cl.
CPC ............ *A61M 25/0009* (2013.01); *A61F 2/04* (2013.01); *A61M 27/008* (2013.01); *B29C 33/02* (2013.01);
(Continued)

(58) Field of Classification Search
CPC .................................. B29C 33/02; B29D 23/00
(Continued)

(56) References Cited

U.S. PATENT DOCUMENTS

| 4,568,338 A | 2/1986 | Todd |
| 4,694,838 A | 9/1987 | Wijayarthna et al. |

(Continued)

FOREIGN PATENT DOCUMENTS

| CA | 3059053 | 10/2018 |
| CN | 108245726 | 7/2018 |

(Continued)

OTHER PUBLICATIONS

"International Search Report and Written Opinion; PCT/US2023/026083".

(Continued)

*Primary Examiner* — Jeffrey M Wollschlager
*Assistant Examiner* — Xue H Liu
(74) *Attorney, Agent, or Firm* — Caldwell Intellectual Property Law

(57) ABSTRACT

A catheter device and manufacturing process for manufacturing the catheter device, wherein the catheter device has a halo-shaped coiled portion extending away from a perpendicular stem portion through a swan neck portion. Eyelets on the halo coil portion and swan neck portion facilitate flow out of the bladder through the catheter device vertical to the catheter, rather than perpendicularly as is the case with existing catheters. The catheter device is formed by using a straight catheter tube, heating and cooling it within a formed mold to have the halo coil and swan neck, such that it can be straightened using a pusher and stylet, inserted into the body while straightened, and thereafter return to its coiled shape when the stylet is removed.

6 Claims, 17 Drawing Sheets

Related U.S. Application Data application No. 17/012,920, filed on Sep. 4, 2020, now abandoned.

(60) Provisional application No. 62/896,724, filed on Sep. 6, 2019.

(51) Int. Cl.
*A61M 25/00* (2006.01)
*A61M 27/00* (2006.01)
*B29D 23/00* (2006.01)

(52) U.S. Cl.
CPC ........ *B29D 23/00* (2013.01); *A61F 2002/047* (2013.01); *A61F 2002/048* (2013.01); *A61F 2210/0014* (2013.01); *A61F 2220/0008* (2013.01); *A61F 2220/0075* (2013.01); *A61F 2230/0091* (2013.01); *A61F 2240/001* (2013.01); *A61F 2240/004* (2013.01); *A61M 2210/1089* (2013.01)

(58) Field of Classification Search
USPC ....................................................... 264/319
See application file for complete search history.

(56) References Cited

U.S. PATENT DOCUMENTS

| | | |
|---|---|---|
| 4,738,667 A | 4/1988 | Galloway |
| 4,834,725 A | 5/1989 | Iwatschenko |
| 4,935,004 A | 6/1990 | Cruz |
| 5,163,928 A | 11/1992 | Hobbs et al. |
| 5,171,227 A | 12/1992 | Twardowski et al. |
| 5,322,501 A | 6/1994 | Mahmud-Durrani |
| 5,518,498 A | 5/1996 | Lindenberg et al. |
| 5,865,815 A | 2/1999 | Tihon |
| 5,876,417 A | 3/1999 | Devinec et al. |
| 5,997,526 A | 12/1999 | Giba et al. |
| 6,053,897 A | 4/2000 | Sachse |
| 6,090,121 A | 7/2000 | Weber et al. |
| 6,589,228 B2 | 7/2003 | Holzer |
| 6,620,202 B2 | 9/2003 | Bottcher et al. |
| 6,743,198 B1 | 6/2004 | Tihon |
| 6,852,105 B2 | 2/2005 | Bolsjoet et al. |
| 7,044,980 B2 | 5/2006 | Hammond et al. |
| 7,662,145 B2 | 2/2010 | Bolmsjo et al. |
| 7,682,401 B2 | 3/2010 | Deal |
| 7,766,899 B2 | 8/2010 | Bolmsjo et al. |
| 8,287,519 B2 | 10/2012 | Smith |
| 8,328,877 B2 | 12/2012 | Gellman |
| 8,430,894 B2 | 4/2013 | Brooks et al. |
| 9,950,138 B2 | 4/2018 | O'Callaghan et al. |
| 10,888,297 B2 | 1/2021 | McDonald |
| 2003/0078467 A1 | 4/2003 | Whalen et al. |
| 2005/0080399 A1 | 4/2005 | Bolmsjo et al. |
| 2006/0111691 A1 | 5/2006 | Bolmsjo et al. |
| 2006/0155250 A1 | 7/2006 | Endo et al. |
| 2006/0178739 A1 | 8/2006 | Shalaby et al. |
| 2007/0049907 A1 | 3/2007 | Fischer, Jr. et al. |
| 2009/0157053 A1 | 6/2009 | Davis et al. |
| 2009/0326560 A1 | 12/2009 | Lampropoulos et al. |
| 2010/0145467 A1 | 7/2010 | Davoudi et al. |
| 2011/0125135 A1 | 5/2011 | Ahmed et al. |
| 2011/0150961 A1 | 6/2011 | Perry et al. |
| 2014/0171921 A1 | 6/2014 | Pearce, III et al. |
| 2014/0336624 A1 | 11/2014 | Adams, Jr. et al. |
| 2015/0088150 A1 | 3/2015 | Lee et al. |
| 2015/0328027 A1 | 11/2015 | Nishio et al. |
| 2015/0352321 A1 | 12/2015 | Hannon et al. |
| 2016/0220784 A1 | 8/2016 | Palmer |
| 2018/0043135 A1 | 2/2018 | Chen et al. |
| 2018/0078462 A1 | 3/2018 | Young |
| 2019/0091442 A1 | 3/2019 | Erbey, II |
| 2019/0099584 A1 | 4/2019 | Erbey, II et al. |
| 2019/0105465 A1 | 4/2019 | Erbey, II et al. |
| 2023/0248938 A1 | 8/2023 | Hazan et al. |

FOREIGN PATENT DOCUMENTS

| | | |
|---|---|---|
| CN | 109276797 | 1/2019 |
| WO | 9618428 | 6/1996 |
| WO | 2018200060 | 1/2018 |
| WO | 2018188781 | 10/2018 |
| WO | 2020097476 | 5/2020 |
| WO | 2021186384 | 9/2021 |

OTHER PUBLICATIONS

"International Search Report and Written Opinion, PCT/US2021/049204".

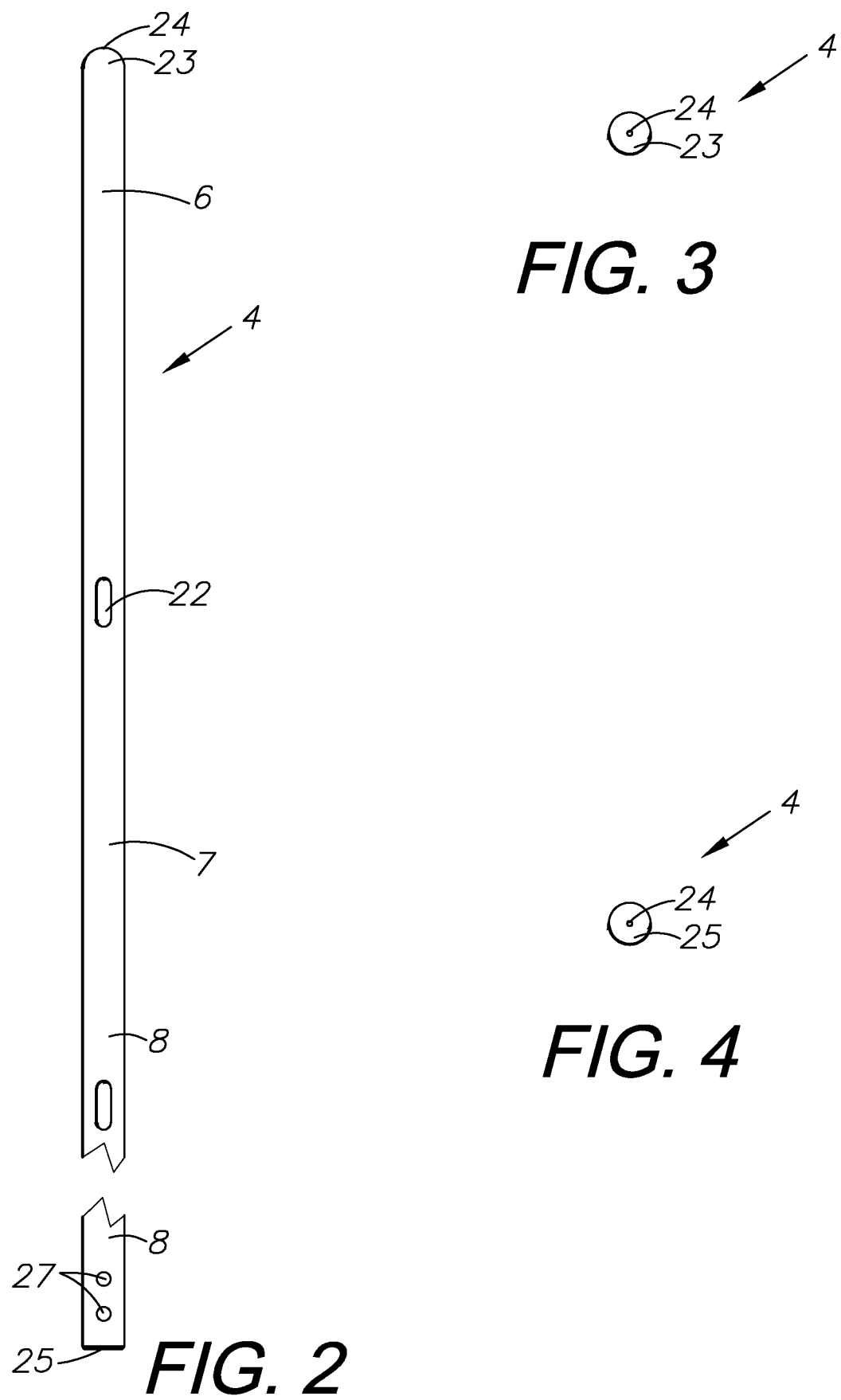

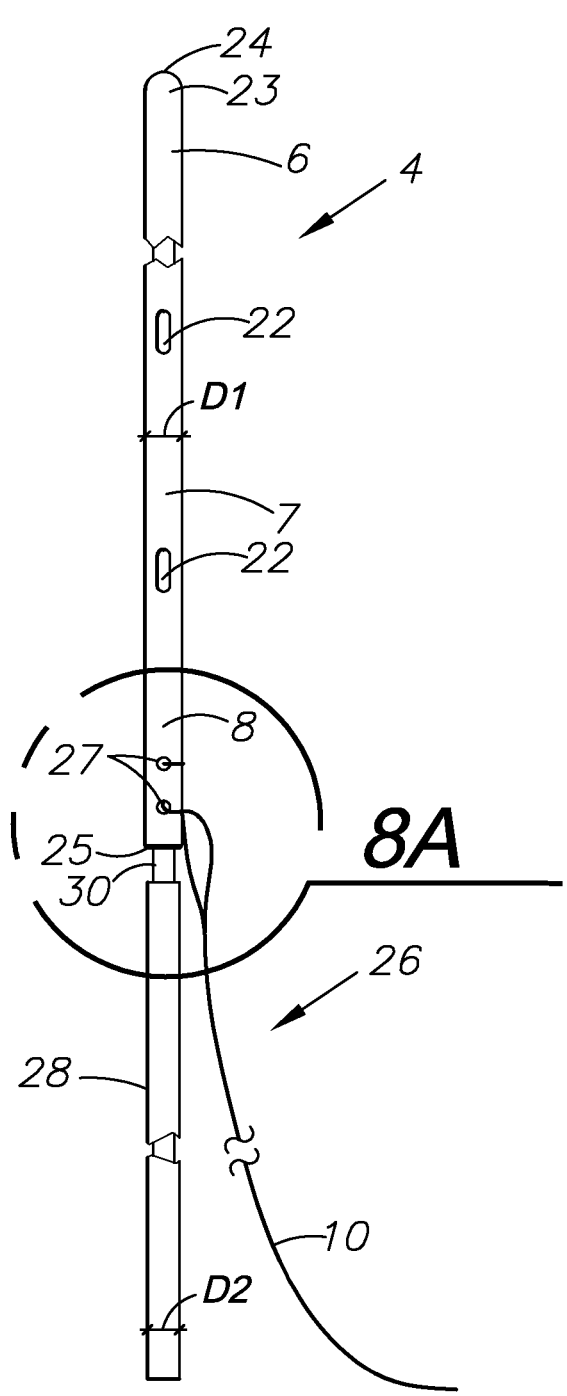
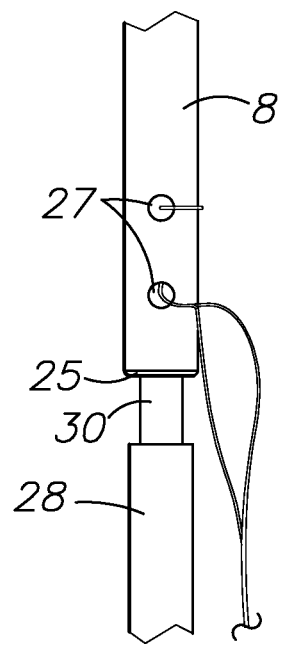
FIG. 8A
FIG. 8

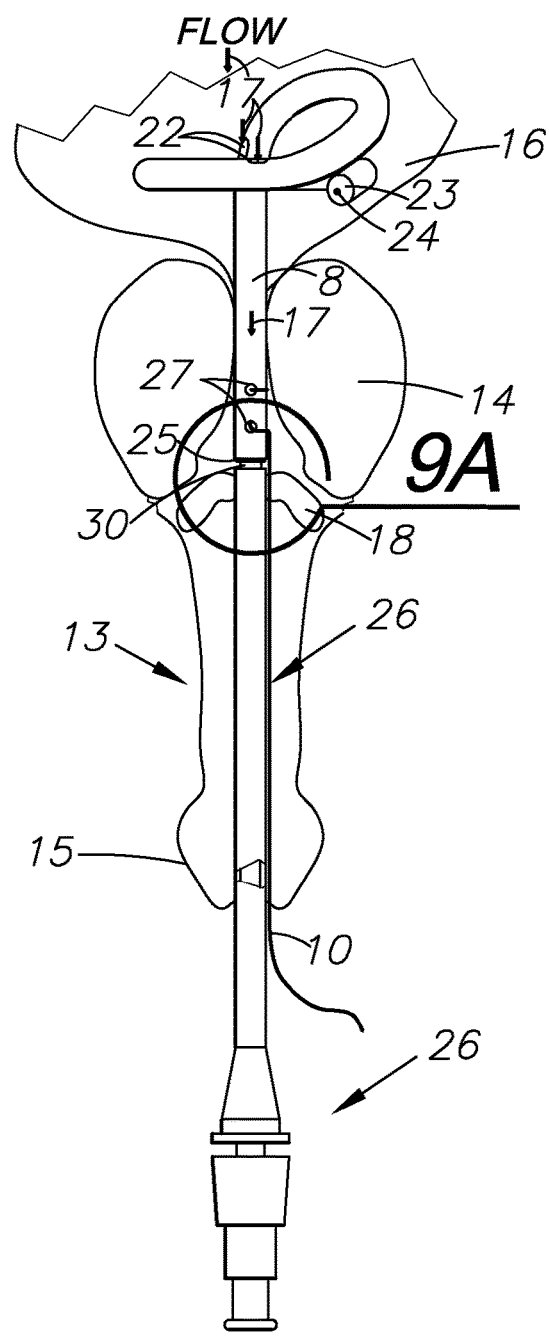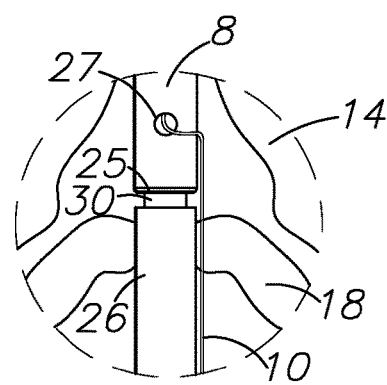
FIG. 9A
FIG. 9

COIL CATHETER METHOD OF MANUFACTURE

CROSS-REFERENCE TO RELATED APPLICATION

This application is a continuation of U.S. patent application Ser. No. 17/850,389, filed Jun. 27, 2022, which is a continuation-in-part of U.S. patent application Ser. No. 17/012,920, filed Sep. 4, 2020, which claims priority in U.S. Provisional Patent Application No. 62/896,724 Filed Sep. 6, 2019, all of which are incorporated herein by reference.

BACKGROUND OF THE INVENTION

1. Field of the Invention

The present invention relates generally to a coil catheter, method for use thereof, and method of manufacture thereof, and more specifically to a catheter having a retention coil member for repositioning, validation of placement, and removal, method of use, and method of manufacture thereof.

2. Description of the Related Art

Urinary retention in males generally implies that urine is produced normally but is retained within the bladder due to primary detrusor dysfunction or an obstruction at or distal to the bladder neck. Prostatic obstruction causes an increased resistance for the passage of urine with subsequent increased pressure on the bladder musculature resulting in two successive phases; 1) compensation, where bladder emptying still takes place, and 2) decompensation, characterized by increasing amounts of residual urine and ultimately urine retention. Bladder outlet obstruction producing urinary retention may result from, including but not limiting, benign prostatic hypertrophy, prostate cancer, or any acute enlargement of the prostate including but not limited to acute prostatitis, post focal procedures on the prostate, radiation, cryotherapy or instrumentation. Urinary retention occurs primarily in males with benign prostatic hypertrophy being the most common cause in men over the age of 50 years. It has been estimated that one in four men in the United States will have been treated for symptomatic benign prostatic hypertrophy by the time they reach 80 years of age.

The prior art contains several examples, including devices which are disclosed in U.S. Pat. No. 7,044,980, incorporated herein by reference. Relevant, but distinguishable, prior art also includes U.S. Pat. No. 4,738,667 which teaches a halo-style catheter which presents additional issues that would need to be solved. For example, existing concepts and systems require external draining and a sheath requiring a bulbous end which was designed, at the time, to avoid stiff guidewires. New guidewires for catheter placement have reduced this stiffness, and are superior to such sheathes as taught in the prior art. What is desirable is a tapered end with a guidewire for ease of placement.

Material choices in existing systems also can be problematic. For example, Dacron (a cloth-like material) is taught by the prior art for use in coating a catheter. This material can become highly lithogenic when exposed to urine, so it would be ideal to use an alternative material or method. Another issue taught in the prior art is a sheath which becomes a permanent part of the system required to straighten the catheter for insertion and is further used to uncoil and retract the catheter from the bladder. It would be desirable to not require a permanently placed sheath to remove additional obstacles from operation of a catheter.

It is also taught through prior systems to transverse the external sphincter of the bladder. This results in incontinence, even though the bladder may be draining through the catheter, because the sphincter is required to be kept open due to the presence of the existing catheters. It is desirable to shorten the upper arm of such a catheter such that it sits above the urinary sphincter rather than retaining that sphincter in an open orientation.

Management for urinary retention related to prostate obstruction involves bladder drainage generally accomplished by placement of a transurethral, suprapubic catheter or intermittent self-catheterization. This creates a passageway between the bladder and the exterior of the body that allows a flow of urine to the outside.

Heretofore there has not been available a system or method for a catheter with the advantages and features of the present invention.

BRIEF SUMMARY OF THE INVENTION

The invention involves facilitating drainage and, more specifically, but not by way of limitation, to facilitating fluid drainage from the bladder and through the urethra of a patient experiencing either acute or chronic urinary obstruction.

The retention member for the device is a coil device which has a straight non coiled iteration for placement. Once placed into the bladder a stylet is removed which allows for the coiled default state to be achieved. The pusher segment is connected during placement and can be utilized for a period of time to collect urine and then removed allowing the device to have only a thread (Monofilament Suture type material) connected externally. The coil tubular portion abutted to the pusher allows for passage and collection of urine. With the disconnection of the pusher segment, the coil catheter allows for the passage of urine without an external tubular structure and external collection device. The converted iteration is from long external catheter to short coil device without the tubular extension thru the sphincter or distal urethra.

In general, and in one aspect, the invention relates to a catheter system, which embodies the ability to control a coil tip catheter within the bladder or body cavity by an attached thread traversing thru the urethra to the exterior. The coil catheter comprises a body member and a coil retaining member. The body member includes a distal terminating end, a proximal end portion, and a lumen extending within the body member to allow fluid drainage through the body member a well as around the tubular segment. Eyelets are placed in the device at but not limited to at the swan neck section and at the proximal coil tip. A guide wire opening at the tip allows for use of a guide wire to facilitate delivery of the device due to urethral or prostate anatomical challenges.

The directional terms proximal and distal require a point of reference. In this application, the point of reference in determining direction is from the perspective of the patient. Therefore, the term proximal will always refer to a direction that points into the patient's body, whereas distal will always refer to a direction that points out of the patient's body.

The body member is sized for placement substantially within the bladder and bladder neck, prostate urethra, with the distal terminating end located proximal to an external urethral sphincter to allow normal operation of the external sphincter. The coil retaining member extends from the proximal end portion of the body member. The coil retaining member is straightened into a first state to allow passage of the catheter into the urethra, and the coil retaining member is coiled into a second state when located in a bladder to hold the body member in place substantially within the urethra by removing a straightening stylet. The pusher segment abuts to the distal tubular segment such that the device does not migrate as the straightening stylet is removed.

Embodiments of this aspect can include the following features. The Coil catheter system is comprised of a coil catheter, a connecting segment, a monofilament suture, and a pusher tubular device. The Coil catheter is comprised of a body member and a proximal coil retaining member. The Swan Neck portion of the coil is the transition from the tubular segment and the coil angles proximally then curves distally into a horizontal portion of the coil. The right angle and swan neck configuration allows for retaining of the device as well as a tolerance to traction prior to removal. The length of the tubular, swan neck and coil can be changed to facilitate a variety of anatomical and gender specific challenges. Multiple coils and a short tubular segment is appropriate for females with short urethra which would allow for catheterization from inside the bladder outward and controlled externally with the control suture. In patients with a dysfunctional sphincter, the device requires bridging the sphincter to empty the bladder then snap back proximal to the sphincter to allow for continence. This is a dynamic catheterization device which passive state in the prostate fossa in men and bladder for females. The default state for spinal cord patients would be proximal to the urinary sphincter with dynamic positioning for bladder emptying bridging the sphincter. Upon bladder drainage in this spinal cord type patient the suture, without gently pulling, will revert back to a position proximal to the sphincter which allows for continence.

The Coil replaces the balloon as a retaining member. The coil consists of a tapered tip with guide wire channel, eyelets placed at various and not limited locations on the coil segment. The eyelet placed in the swan neck is perpendicular to the direction of flow. The bladder mucosa trauma is minimized due to the placement of the eyelets. The curve of the coil is fashioned to have a "swan neck" portion which extends from the horizontal plane of the coil device which is a right angle to the tubular portion. The "Swan Neck" portion allows for some allowance for traction on the device prior to uncoiling of the horizontal member. While the inadvertent removal of an inflated balloon type catheter results in urethral mucosal injury, catheter mucosal injury is minimized if inadvertent removal of the Coil occurs, since the diameter of the device at removal is the same as upon insertion.

The coil retaining member of the coil catheter can be a tube constructed with coil-shape memory. The coil retaining member also can be rounded at the ends of the tubing to provide user comfort during insertion of the catheter into the patient's urethra. A guide wire channel allows for a guide wire to be utilized with difficult placement due to false passages in the urethra or other anatomical challenges.

The process for creating the swan neck vertical dynamic portion of the device with a horizontal coil is a unique process encompassing features defined in the Utility patent identified as Manufacturing Process for integration of retaining member with vertical component coupled with the horizontal coil. The Vectors of pull impact the device in two separate phases of uncoiling, they are coupled with a resistance to pull out which is initially absorbed by the vertical swan neck component.

Prior to and during insertion of the coil catheter into the patient's urethra, the coil retaining member is in a straightened first state. The coil retaining member returns to substantially the second coil state once in the patient's bladder and thereby acts as an anchor to keep the body member of the catheter substantially within the prostatic urethra.

In one embodiment, the body member can include one or more side openings to allow fluid to drain from the urethra. The lumen of the body member and length of the tube can be designed to be equivalent to a variety of tubular dimensions. One embodiment would include a tubular portion which is constructed to have a star shaped exterior which allows urine to travel predominantly around rather than thru the device.

In one embodiment, the suture should be long enough to extend from the body member to the outside of the patient's body. The suture can also be comprised of monofilament nylon or other equivalent materials. The coil catheter can be removed easily from the patient's body by pulling downward on the suture. The end of the suture can be connected to a structure (e.g., snap cap, ball, ring, coil) that extends out of the body entirely. The purpose of the snap cap is to facilitate location of the suture's end and eventual removal of the coil catheter by simply pulling on the located suture. Gentle traction on the suture. In patients with diminished manual dexterity, a magnet can be placed on the snap cap and on the end of the stylet device. This allows for engaging the snap cap with gentle traction and is placed on the device to engage the device into the bladder in females or traverse the sphincter in male patients with sphincter resistance.

The device may utilize additional materials which would add qualities such as, but not limited to, lubrication, hydrophilic coating, radiographic enhancing material. The material for the device is, but not limited to, Carbothane and not limited to ID and OD various stiffness of the material. The Pusher, stylet and suture material are not limited in size or characteristics.

In another embodiment, the invention relates to a Coil catheter system for draining fluid from a patient's body cavity including but not limited to bladder, stomach, colon, ileal loop, colostomy, and abdominal peritoneal cavity.

In general, in still another aspect, the invention allows for the manipulation of a variety of devices within the body cavity to be controlled externally with a tethering suture. This allows for episodic movement from a passive state of the device to an active state, which changes the fluid dynamics to favor voiding or continence. To void, the user pulls on the suture, causing the distal end of the coil to move into the bladder neck and through the sphincter valve, allowing the bladder to drain.

In another device iteration, the device can be fashioned to have an inverted umbrella membrane, which occludes the bladder neck, allowing continence to be achieved.

Another iteration includes the capability of the coil being imbedded with various medications which allows for a unique drug delivery into body cavities such as, but not limited to, the bladder, stomach, colon, ileal loop, colostomy or abdominal cavity. The tethered control also allows for manipulation of the device in the cavity. The device may be configured with monitoring devices allowing for the wireless transmission of images or data.

In another embodiment, the catheter is used for cervical dilation to induce labor.

In yet another embodiment, the catheter is used for widening the nasal passages to treat sleep disorders (e.g., sleep apnea).

The Coil Catheter allows the bladder to fill and contract in synchronous sphincter relaxation without Prostate Urethral resistance. This allows for defining the functional capacity of both the bladder and urinary sphincter. In patients with chronic over distension due to prostate obstruction, the device acts as a Bladder Rehabilitation Device as well as bladder neck and prostate fossa dilation. With acute urinary or chronic retention, the improvement in bladder muscular contraction in a volitional manner may obviate the need for a variety of interventional procedures, which focus on only reduction in Prostate resistance but do nothing to enhance the Vesicular (Bladder) Pressure, which when coupled with reduction in the prostate resistance increases the Flow Rate in patients. More efficient voiding, with reduced residual urine in the bladder, coupled with a competent urinary sphincter and elimination of the need for an external collection device results in a collage of clinical improvements.

The coiled shape has been utilized in a variety of medical devices to resist removing of a straight tubular device. The unique feature of the current vertical and horizontal design with the horizontal portion is distal to the Apex of the device. Proximal is inward toward the patient and distal is the direction away from the patient. Prior coiled shapes were an extension proximal to the tubular device. With tension on these designs the uncoiling began with any tension on the distal tubular portion. The current design protects the uncoiling of the horizontal component from the initial tension. The "swan neck" portion allows for lengthening of the vertical tubular component and with release of the tension will "snap back" to its original position due to the horizontal stabilizing effect. The distance for the extension and snap back allows for a variety of medical applications with innate resistance to inappropriate migration which is common in "pig tail curl" or "J" shaped tips. The application defines the unique manufacturing process to construct the vertical—swan neck—horizontal shaped device.

BRIEF DESCRIPTION OF THE DRAWINGS

The drawings constitute a part of this specification and include exemplary embodiments of the present invention illustrating various objects and features thereof.

FIG. 2 is a front elevational view of a preferred embodiment of the present invention shown in a straightened orientation.

FIG. 3 is a top plan view thereof.

FIG. 4 is a bottom plan view thereof.

FIG. 8 is a front elevational view of a preferred embodiment of the present invention in combination with a typical pusher device.

FIG. 8A is a detailed view of a portion thereof taken about the circle 8A in FIG. 8.

FIG. 9 is a diagrammatic representation thereof shown in a typical environment with an external container.

FIG. 9A is a detailed view of a portion thereof taken about the circle 9A in FIG. 9.

DETAILED DESCRIPTION OF THE PREFERRED EMBODIMENTS

I. Introduction and Environment

As required, detailed aspects of the present invention are disclosed herein, however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed structure.

Certain terminology will be used in the following description for convenience in reference only and will not be limiting. For example, up, down, front, back, right and left refer to the invention as orientated in the view being referred to. The words, "inwardly" and "outwardly" refer to directions toward and away from, respectively, the geometric center of the aspect being described and designated parts thereof. Forwardly and rearwardly are generally in reference to the direction of travel, if appropriate. Said terminology will include the words specifically mentioned, derivatives thereof and words of similar meaning.

The directional terms proximal and distal require a point of reference. In this application, the point of reference in determining direction is from the perspective of the patient. Therefore, the term proximal will always refer to a direction that points into the patient's body, whereas distal will always refer to a direction that points out of the patient's body.

II. Preferred Embodiment Catheter System 2

Figure 1:
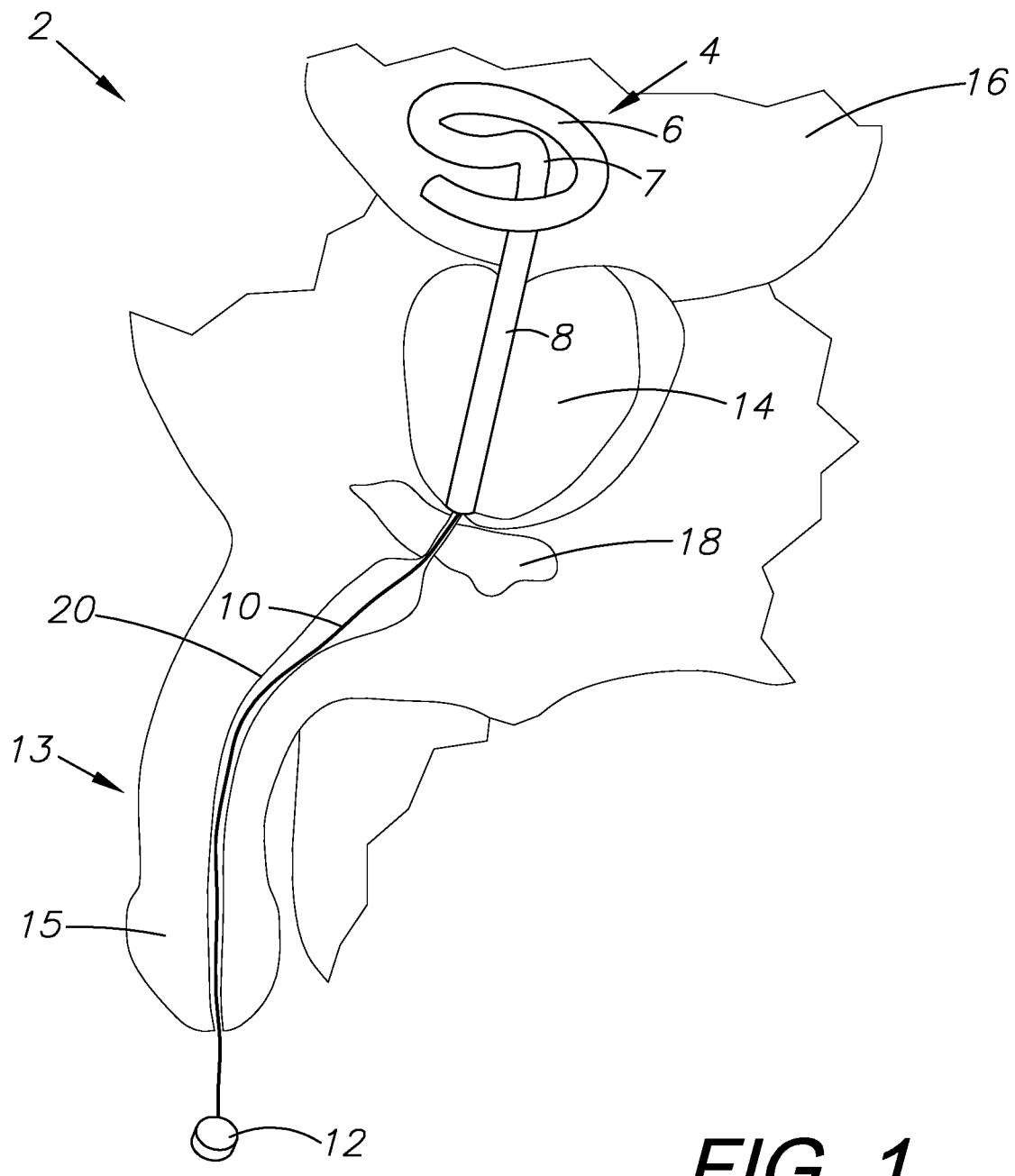
FIG. 1 is a diagrammatic representation of a preferred embodiment of the present inventions shown in a typical environment.

As shown in a typical environment in FIG. 1, the present invention is a catheter system 2 which features a coiled catheter 4 having a halo portion 6 connected to a stem portion 8 via a swan neck bend 7 such that the halo portion is along a plane perpendicular to the direction of the stem portion. The halo portion 6 is located within the bladder 16 once properly placed, and serves to provide optimal flow out of the catheter 4 through the stem 8. FIG. 1 shows a thread 10 connected to a snap cap 12 located outside of the body to prevent the thread 10 from being drawn up into the body, and instead would be stopped at the glans 15 of the penis 13 (as shown). This would function similarly in a female patient. The thread would be formed from a monofilament suture-type material in a preferred embodiment. The snap cap 12 may include a magnet or be made of magnetic material.

The catheter 4 stem 8 passes through the prostate gland 14 and the end of the stem is located in proximity with the external sphincter 18. This system facilitates flow from the bladder 16 through the catheter 4 via eyelets 22, located at least at the swan neck section 7 and at the proximal coil tip 23 of the coil portion 6, and out through the urethra 20 (see FIG. 2). It is important that the stem 8 functions as a short straight arm that un-obstructs the prostatic urethra and sits above the urinary sphincter 18. It does not retain the urinary sphincter in an open orientation ever. This allows for volitional voiding of the bladder by the patient, facilitated by the internal catheter 4, without incontinence.

As shown in FIG. 1, when the catheter 4 is inserted into the bladder, the coil portion 6 coils, forming the swan neck portion which terminates into a right-angle bend which together form a stabilizing elbow which ensures the catheter remains properly in place within the bladder for optimal drainage through the catheter.

FIGS. 2-4 show how the catheter 4 would be inserted into the body in a straight orientation for easy placement. A guidewire hole 24 is located at the tip 23 of the coil portion 6 and at the base 25 of the stem portion 8 for use with a pusher 26 and stylet 30 as is typical. As shown in FIG. 2, the tip 23 is tapered for easy insertion.

Figure 5:
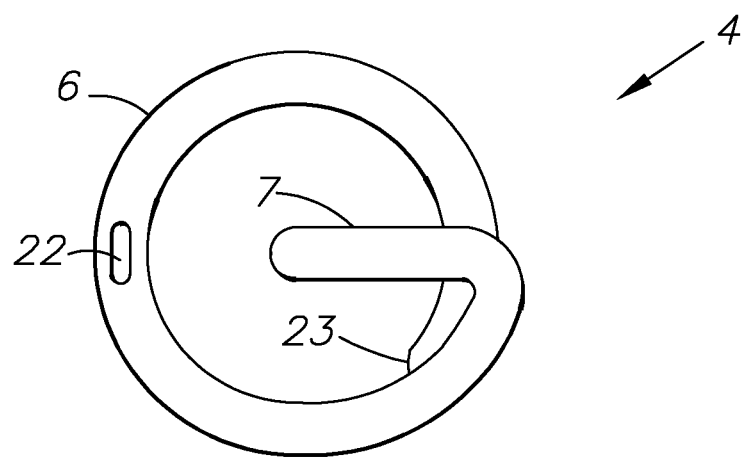
FIG. 5 is a top plan view of a preferred embodiment of the present invention in a coiled orientation.
Figure 6:
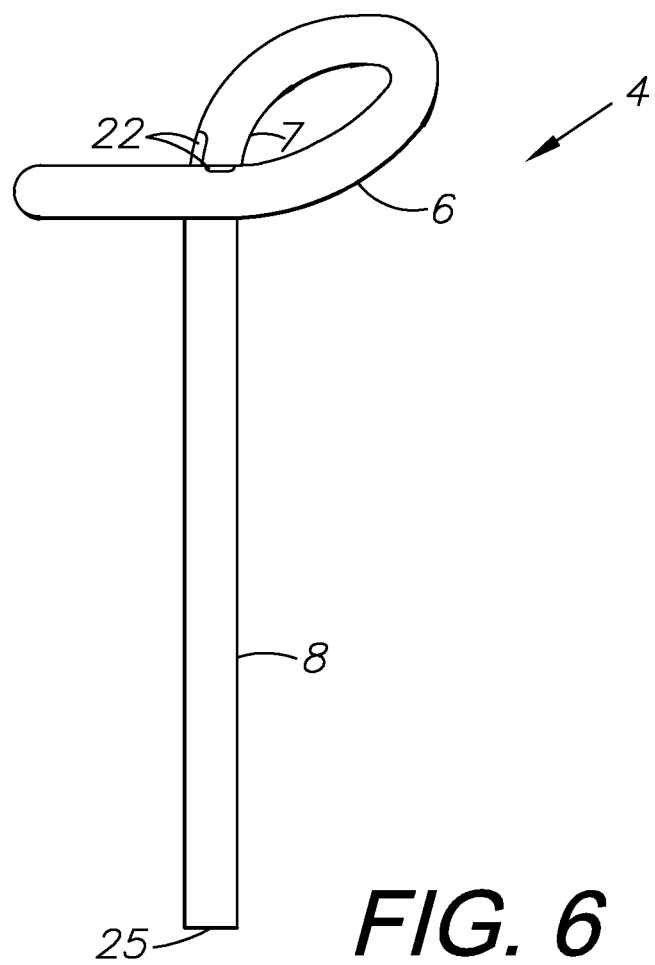
FIG. 6 is a front elevational view thereof.
Figure 7:
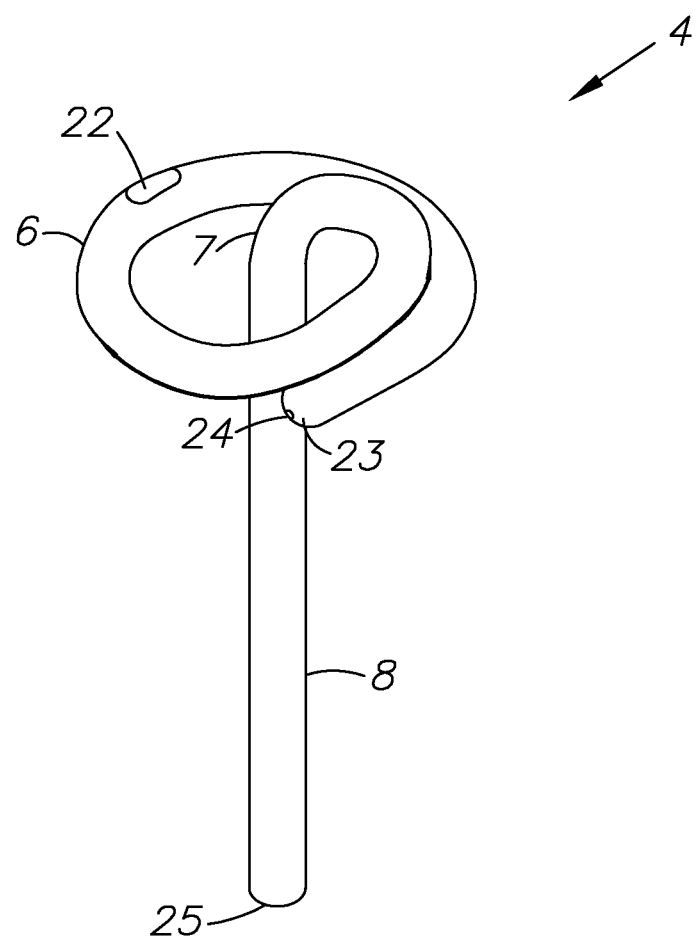
FIG. 7 is a three-dimensional isometric view thereof.

FIG. 5-7 show how the catheter 4 forms into a coiled catheter with a halo portion 6 and swan neck 7 connecting to the stem portion 8 once inserted into its proper environment in the bladder 16. The catheter 4 defaults to this form due to a manufacturing process discussed below. Once the guidewire of the stylet 30 and pusher 26 elements is removed or at least withdrawn slightly, the catheter 4 will automatically coil into the form shown.

FIGS. 8 and 8A show the catheter 4 in its straight orientation in combination with a pusher 26 having an outer tube 28 and a stylet 30. The thread 10 and snap cap 12 extend through the pusher 26 and connect to the end of the catheter 4 near its base 25, shown in more detail in FIG. 11. These figures also show how the pusher 26 has a smaller diameter than that of the catheter 4, further easing insertion of the catheter.

FIG. 9 shows the catheter 4 and pusher 26 in the typical environment shown in FIG. 1 where the catheter is fully inserted and coiled in position. Flow 17 is indicated via the arrows through the catheter 4 by way of eyelets 22, vertically downward rather than perpendicular to the catheter as is the case with prior art catheters. The detailed view of FIG. 9A shows how the thread 10 is retained through receivers 27 in the catheter stem portion 8 to secure the thread to the catheter 4 for removal. The thread is shown external to the pusher 26, which abuts the base 25 of the catheter 4 with the stylet 30 making contact with the base of the stem portion 8 thereof.

Figure 10A:
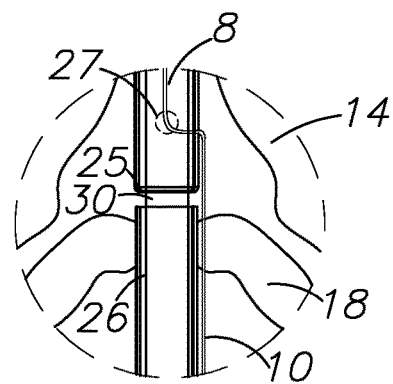
FIG. 10A. is a detailed view of a portion thereof taken about the circle 10A in FIG. 10.
Figure 10:
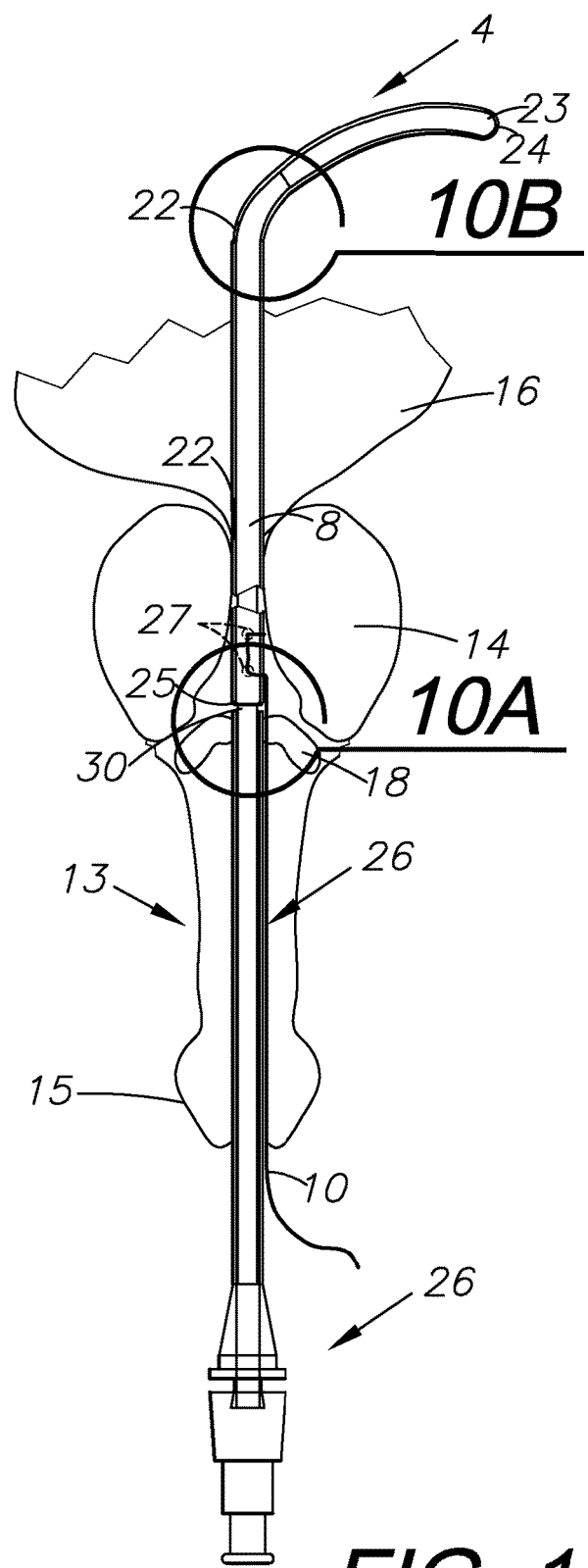
FIG. 10 is a diagrammatic representation thereof shown without an external container.
Figure 10B:
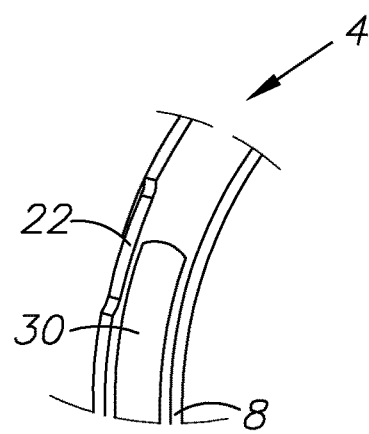
FIG. 10B is a detailed view of a portion thereof taken about the circle 10B in FIG. 10.

FIG. 10 shows the insertion of the catheter 4 using the pusher 26 in a sectional view so as to better show the internal components thereof. FIGS. 10A and 10B show additional detail about their respective circles in FIG. 10, such as FIG. 10B showing how the stylet 30 of the pusher is a functional guidewire that can be placed up and into the catheter itself to help position it within the bladder. The catheter 4 is straightened by the internally placed stylet 30 with guidewire. The catheter as shown is placed over the guidewire for safe insertion into the bladder, after which the guidewire and stylet are removed leaving only the coiled and unencumbered catheter 4 in the bladder as shown in FIG. 1.

Figure 11:
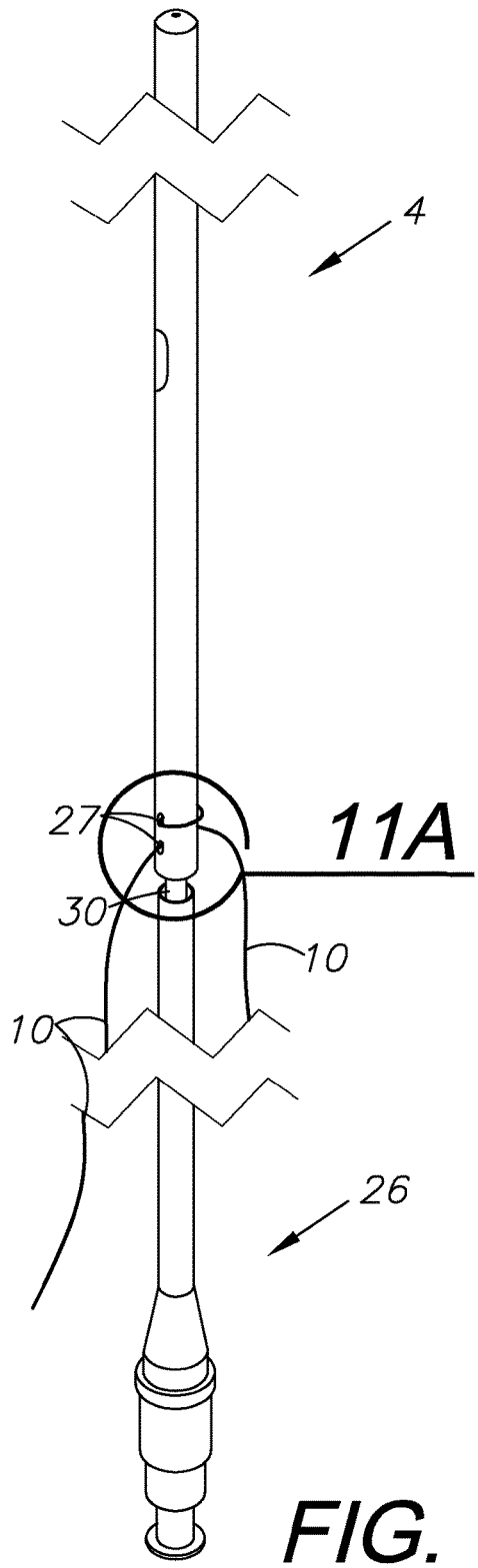
FIG. 11 is a three-dimensional view showing the preferred embodiment of the present invention in combination with a pusher.
Figure 11A:
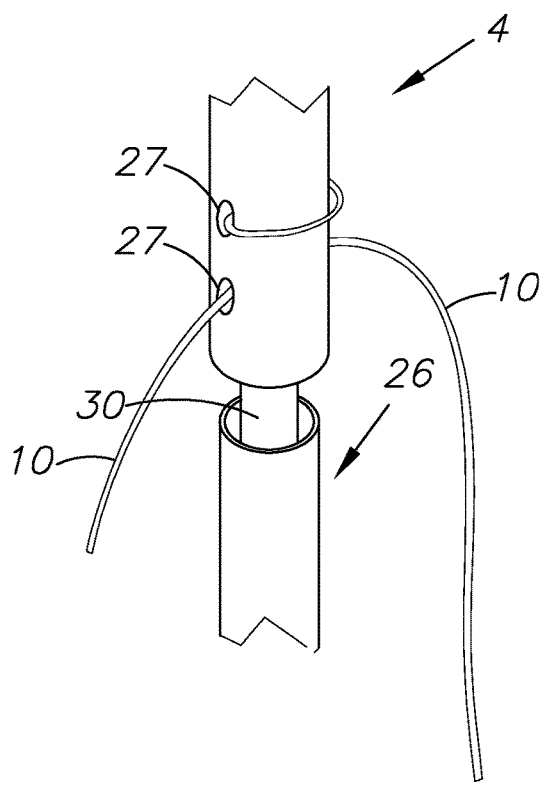
FIG. 11A is a detailed view of a portion thereof taken about the circle 11A in FIG. 11.
Figure 12:
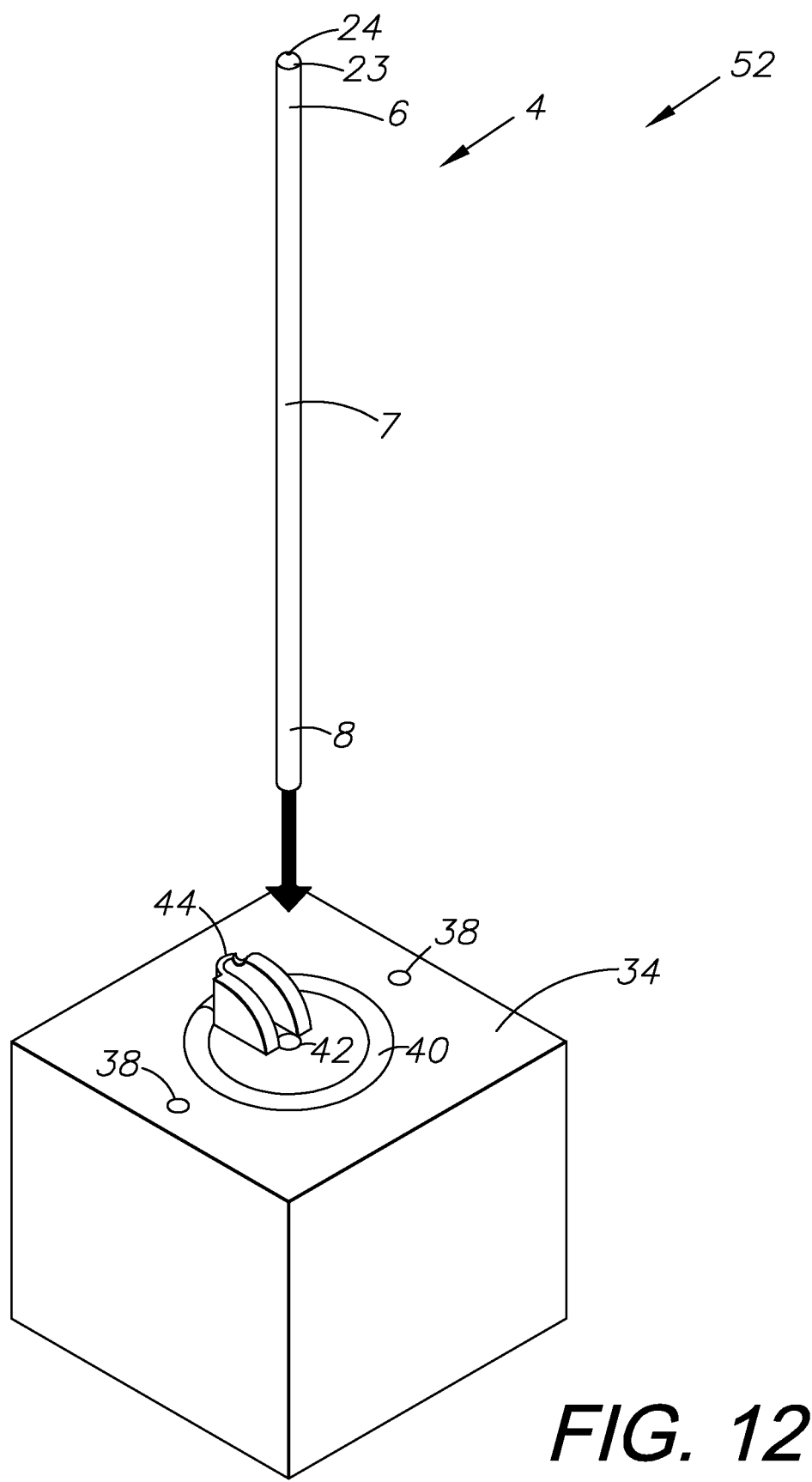
FIG. 12 is a three-dimensional view showing a manufacturing step for manufacturing a preferred embodiment of the present invention.
Figure 13:
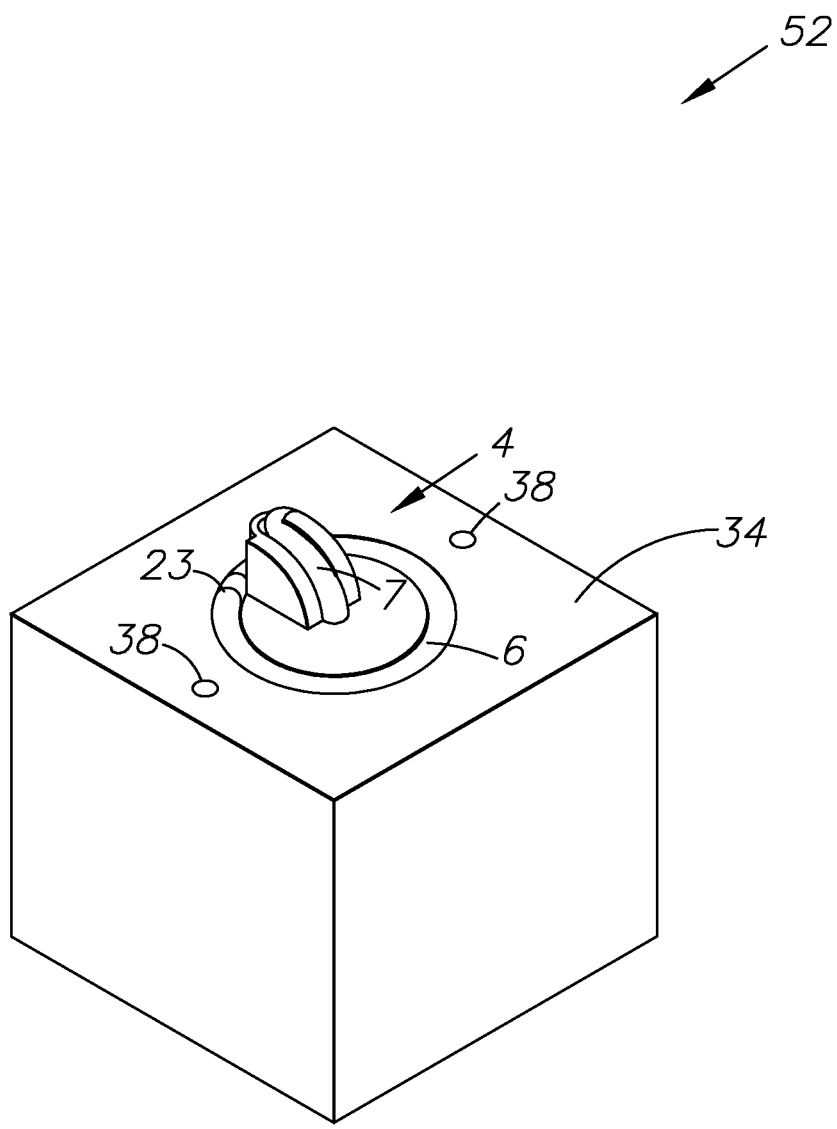
FIG. 13 is a three-dimensional isometric view showing a second manufacturing step thereof.

FIG. 11 and FIG. 11A show in more detail the extraluminal suture thread 10 which does not obstruct the lumen of the catheter 4. Like the positioning of the stem 8 about the sphincter 18, this is intended to prevent incontinence and is used to safely remove the catheter at a later date. No sheath is required for such procedure.

III. System 52 for Manufacture of Catheter System 2

Figure 14:
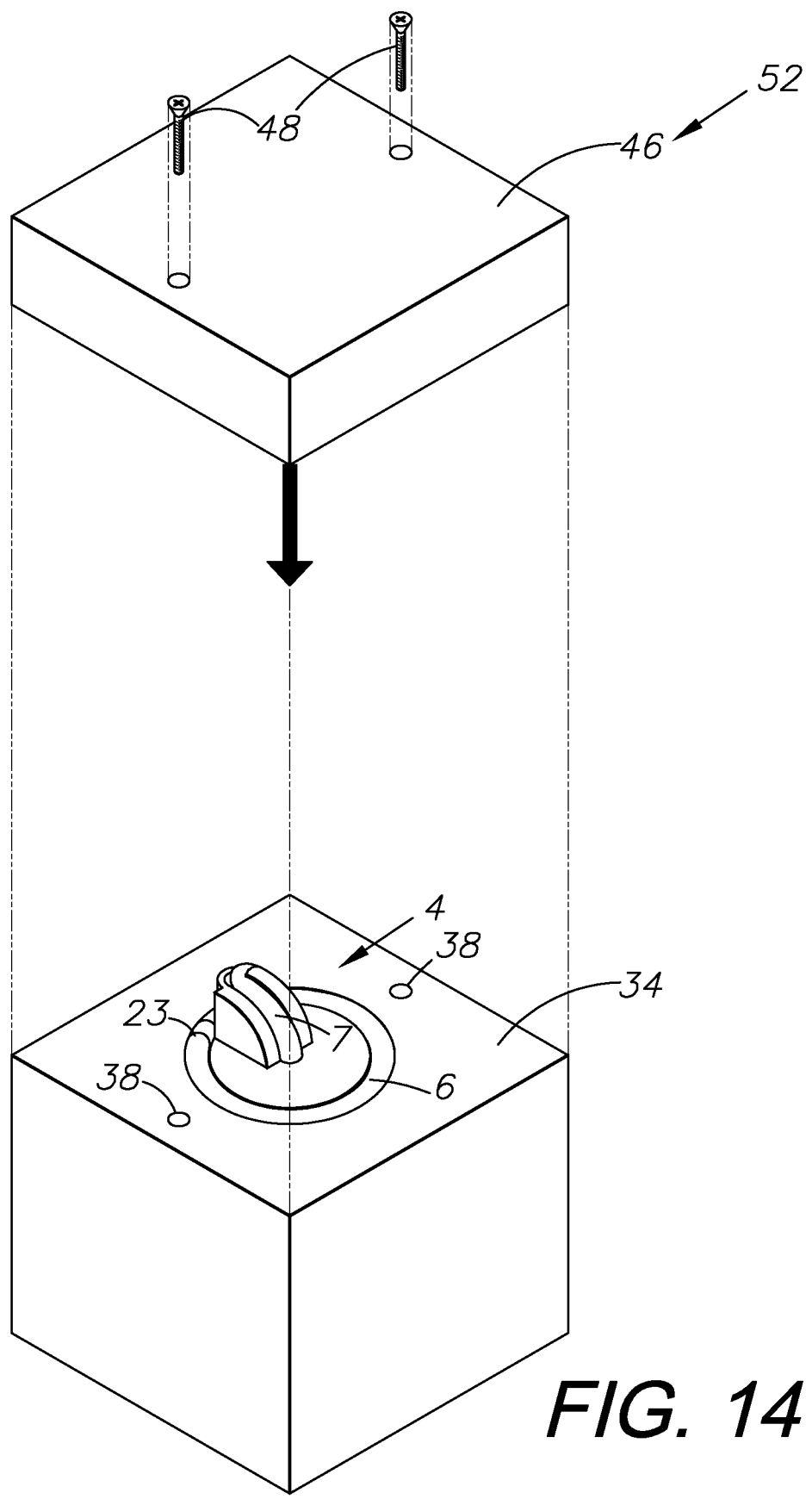
FIG. 14 is a three-dimensional isometric view showing a third manufacturing step thereof.

FIGS. 12-18 show a manufacturing system 52 for manufacturing the coil catheter 4. As shown, the coil catheter 4 is formed from an originally straight catheter tube by placing it into a mold base 34. A flexible yet solid tubing support may be inserted into the catheter tubing prior to molding to prevent kinks during the forming process. The mold base 34 has receiver slots 38 for screws 48 to receive the mold cap 46 as shown in FIG. 14. The mold base 34 also has a forming block with a swan neck form 44 and halo form 40. The stem 8 is inserted into the stem receiver 42 and the swan neck 7 portion is placed into the swan neck form 44, and the halo portion 6 is curled around in the halo form 40. The mold cap 46 is then secured to the mold base 34 via the screws 48.

Figure 15:
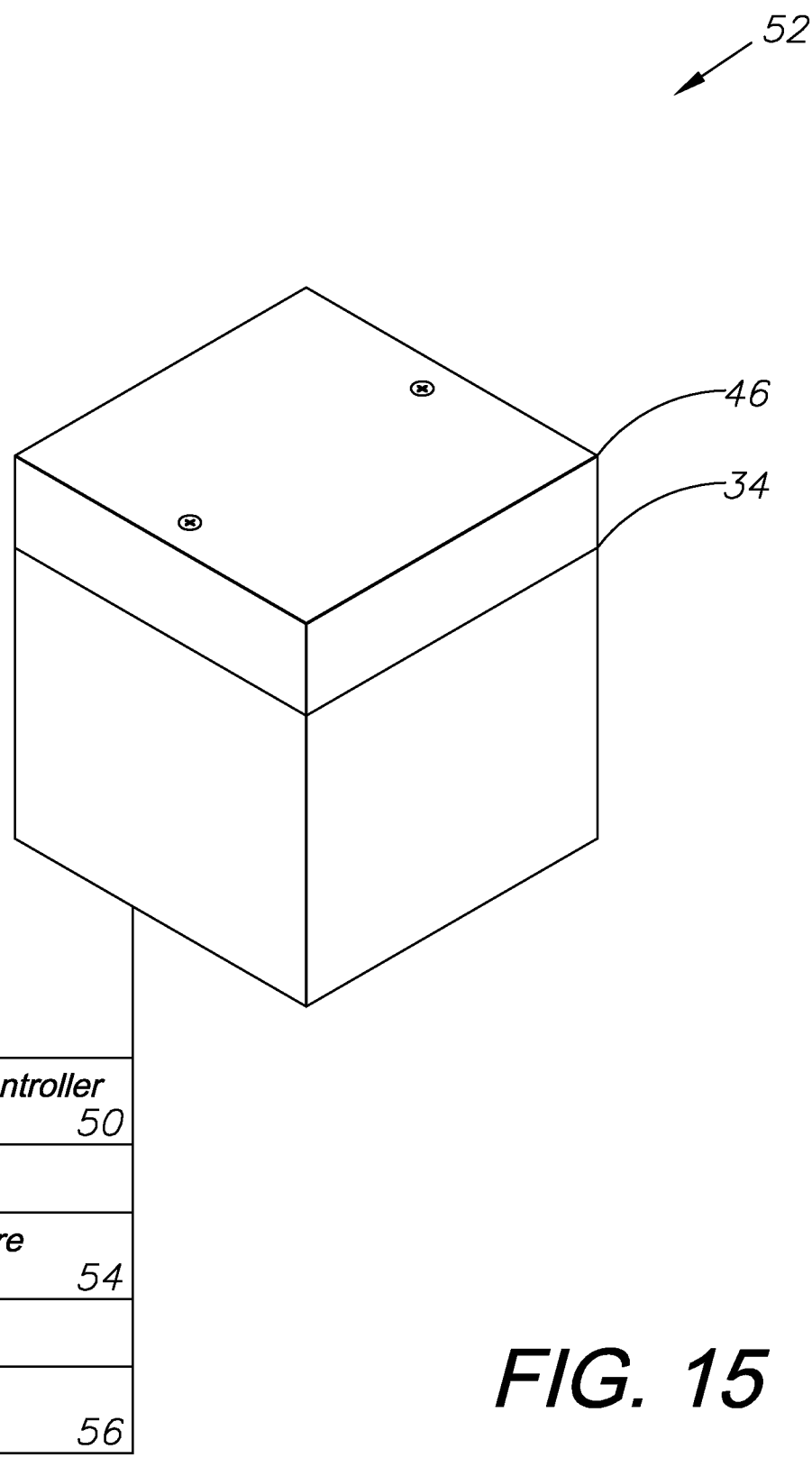
FIG. 15 is a three-dimensional isometric view showing a fourth manufacturing step thereof.
Figure 16:
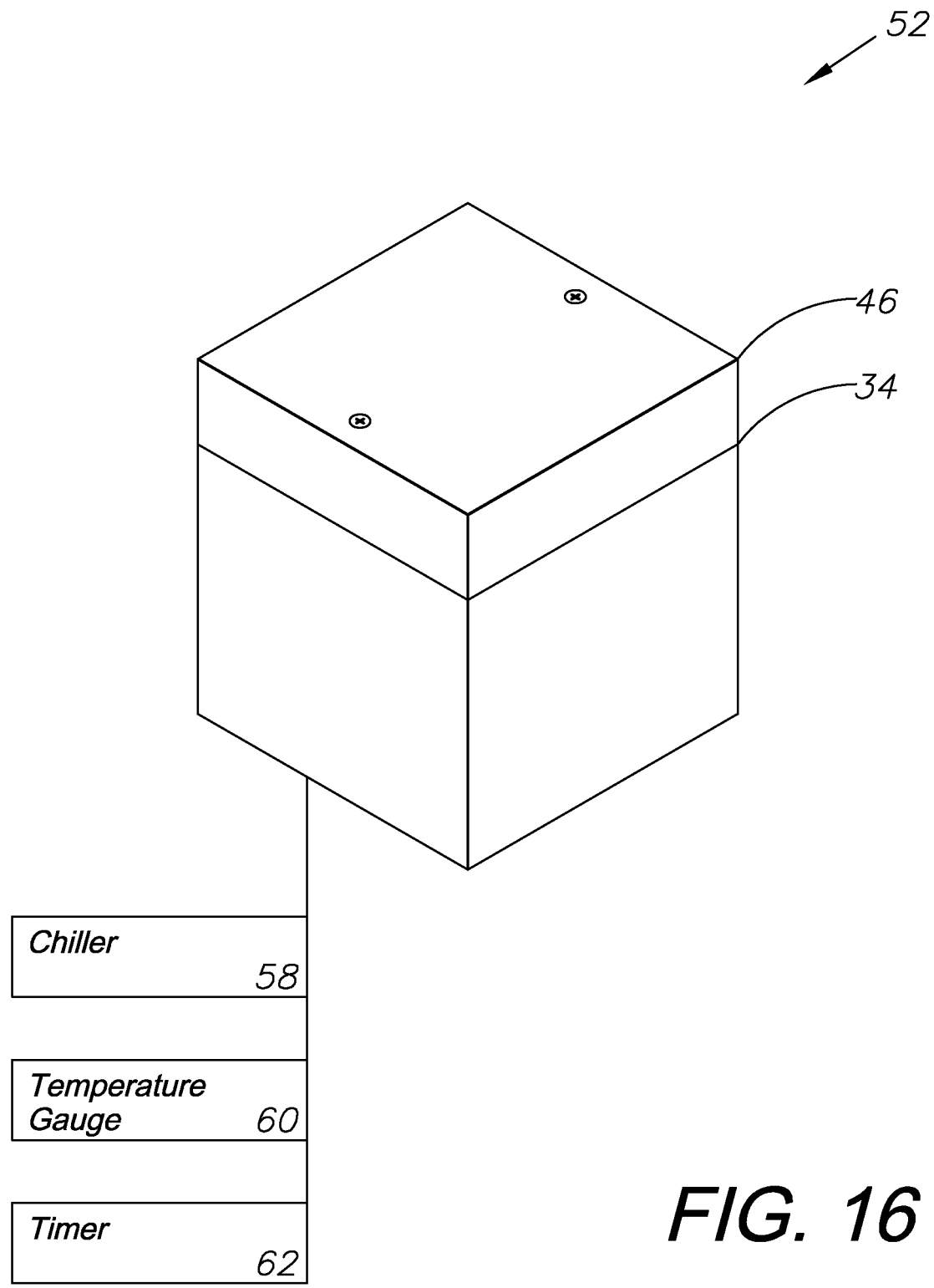
FIG. 16 is a three-dimensional isometric view showing a fifth manufacturing step thereof.

FIG. 15 shows a heating controller 50 with a temperature gauge 54 and timer 56. The mold is heated to an appropriate level to thermoset the coil catheter 4. This process can take approximately 15-19 minutes to reach the proper temperature, at which the mold 34 is held a that temperature for 15 minutes. FIG. 16 shows a chiller 58 with a temperature gauge 60 and timer 62. The chiller 58 sets a temperature of 5.00 degrees Celsius and cools the heated coil catheter 4 down to thermoset its shape. A temperature alarm may be included to properly track chilling. Once the temperature gauge 60 indicates a temperature less than 80 degrees Fahrenheit, typically after 15-19 minutes, the chiller 58 is turned off.

Figure 17:
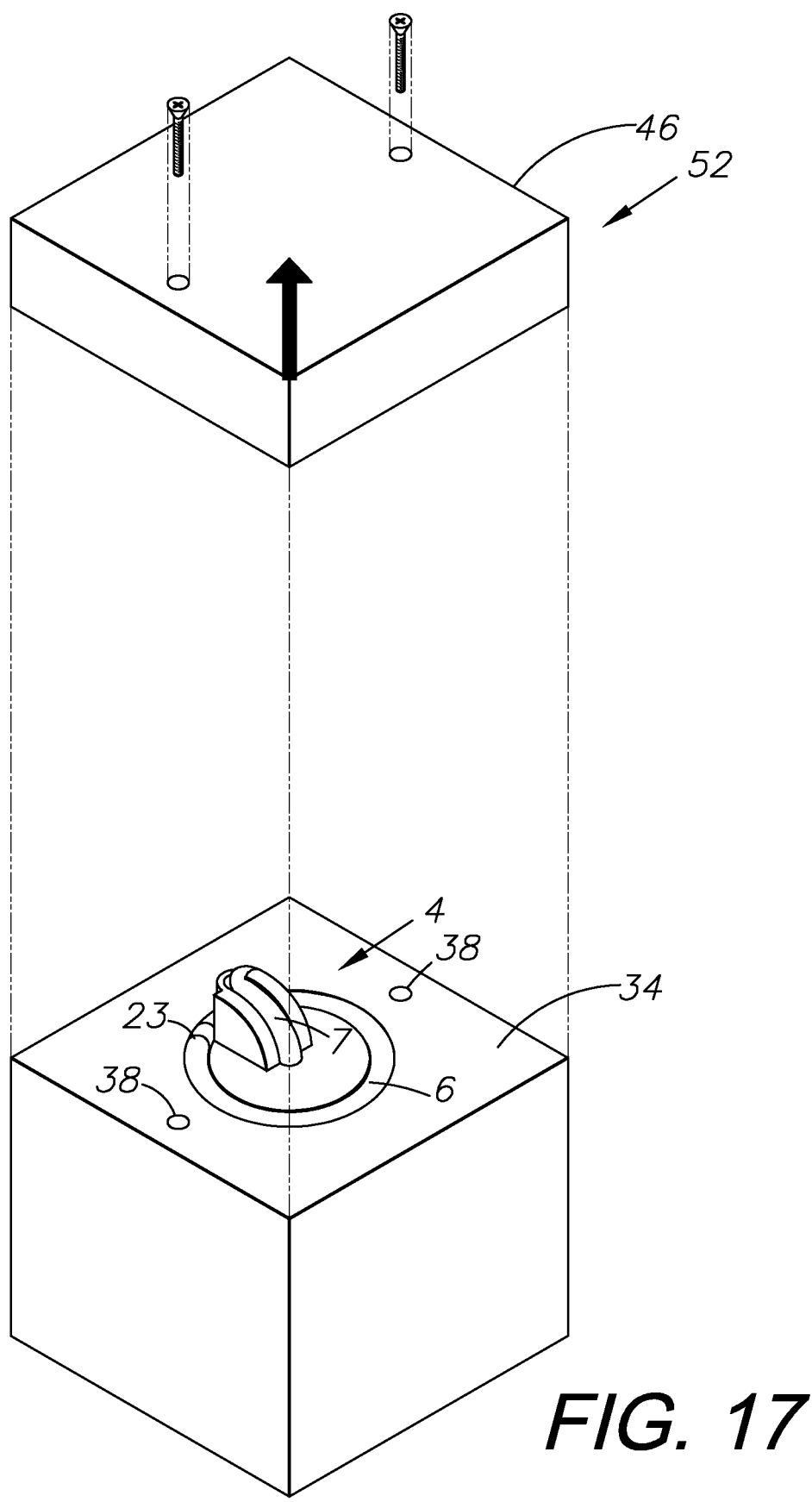
FIG. 17 is a three-dimensional isometric view showing a sixth manufacturing step thereof.
Figure 18:
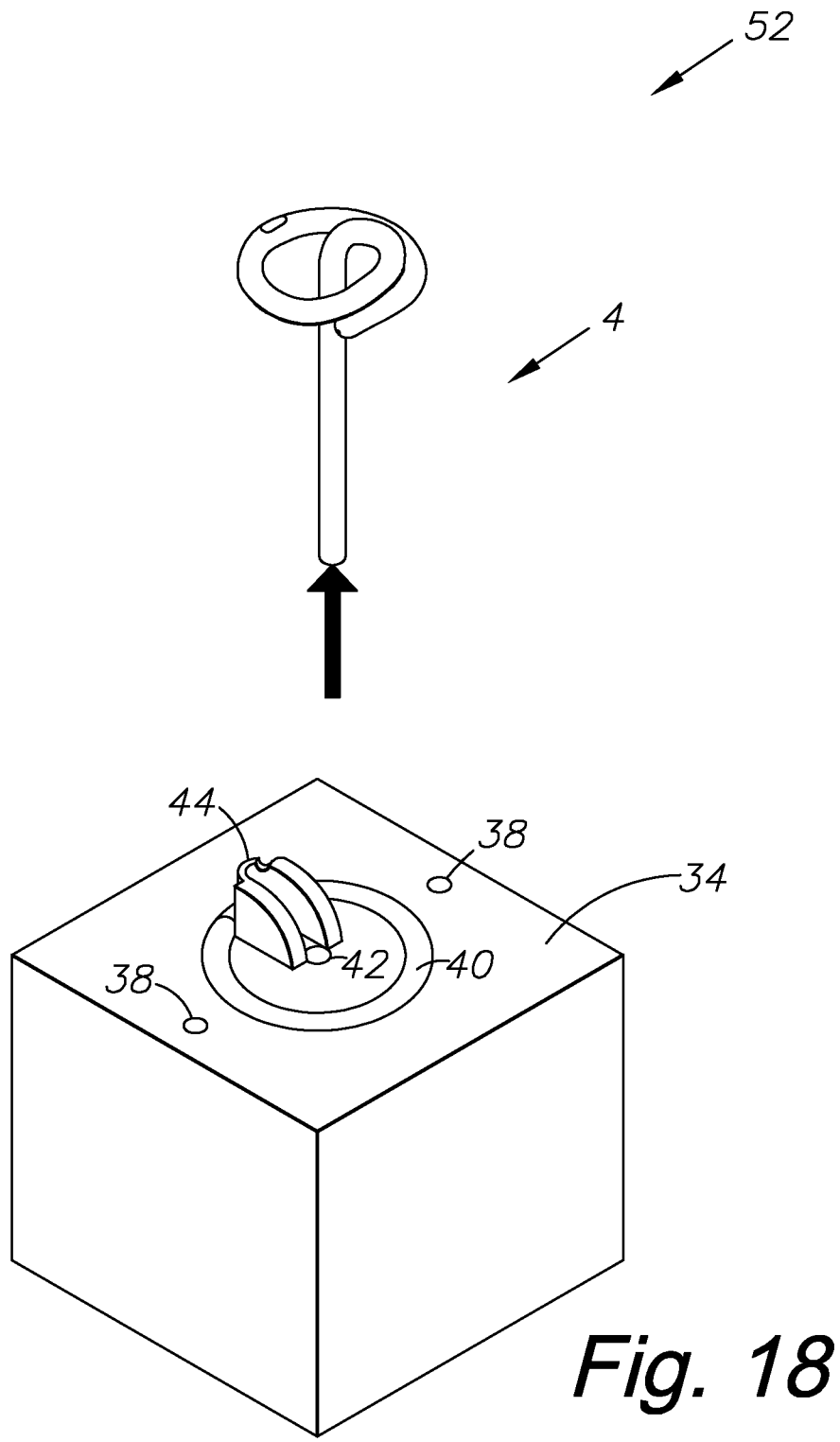
FIG. 18 is a three-dimensional isometric view showing a seventh manufacturing step thereof.

The mold cap 46 is removed as shown in FIG. 17 and the thermoset coil catheter 4 is removed from the mold base 34 as shown in FIG. 18. After this step, the coil catheter 4 can be placed on a rack for further cooling and should be covered to reduce contamination risks.

IV. Method 102 of Using Catheter System 2

Figure 19:
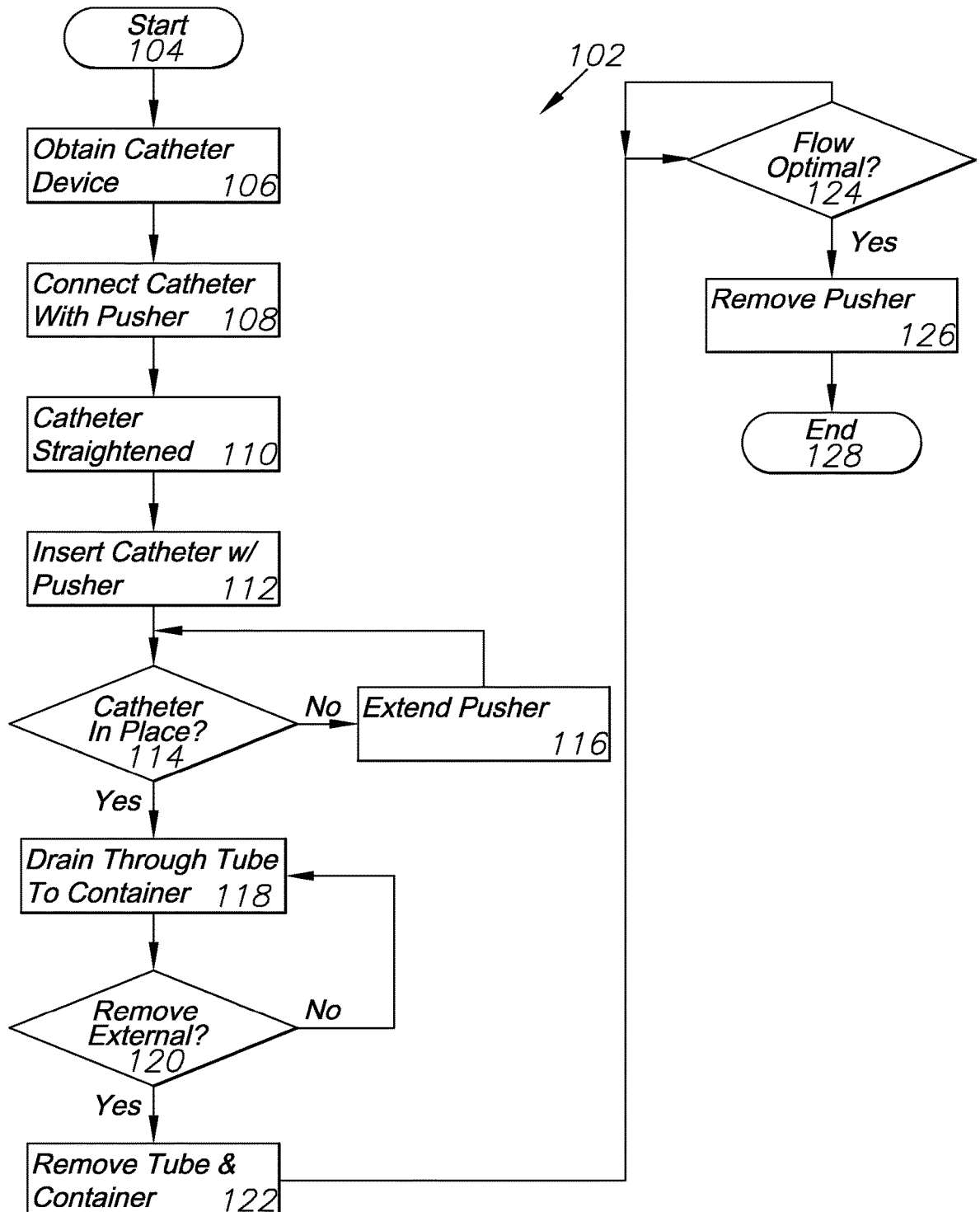
FIG. 19 is a flow chart diagramming the method of using a preferred embodiment of the present invention.

FIG. 19 shows the steps taken in practicing a method 102 of using the coil catheter 4 system 2 as described above. The process starts at 104, where the catheter 4 is obtained at 106. A pusher 36 is obtained and used with the catheter at 108, and the catheter 4 is straightened as shown in FIG. 8 at 110. This allows the catheter 4 to be inserted into the body at 112 using the pusher 36. A check of whether the catheter is in place at 114 may require the pusher 36 to be extended at 116 to ensure proper placement of the catheter. Once in place at 114, the bladder will drain through the catheter 4 eyelet 22 into the catheter 4, out through the pusher 36, through a connected tube 27 and into an external container 29 at 118. A determination is made at 120 whether to remove the tube and external container. If not, they remain in place. If so, then the tube and container are removed at 122.

A check is then made at 124 and a determination made whether flow is optimal with the pusher 36 in place. If not, the pusher will remain. If so, the pusher can be removed at 126 so that flow is entirely facilitated using the catheter 4 in the body. The process then ends at 128 until such a time that the catheter is to be removed.

V. Method 152 of Manufacturing System 52 for Manufacture of Catheter System 2

Figure 20:
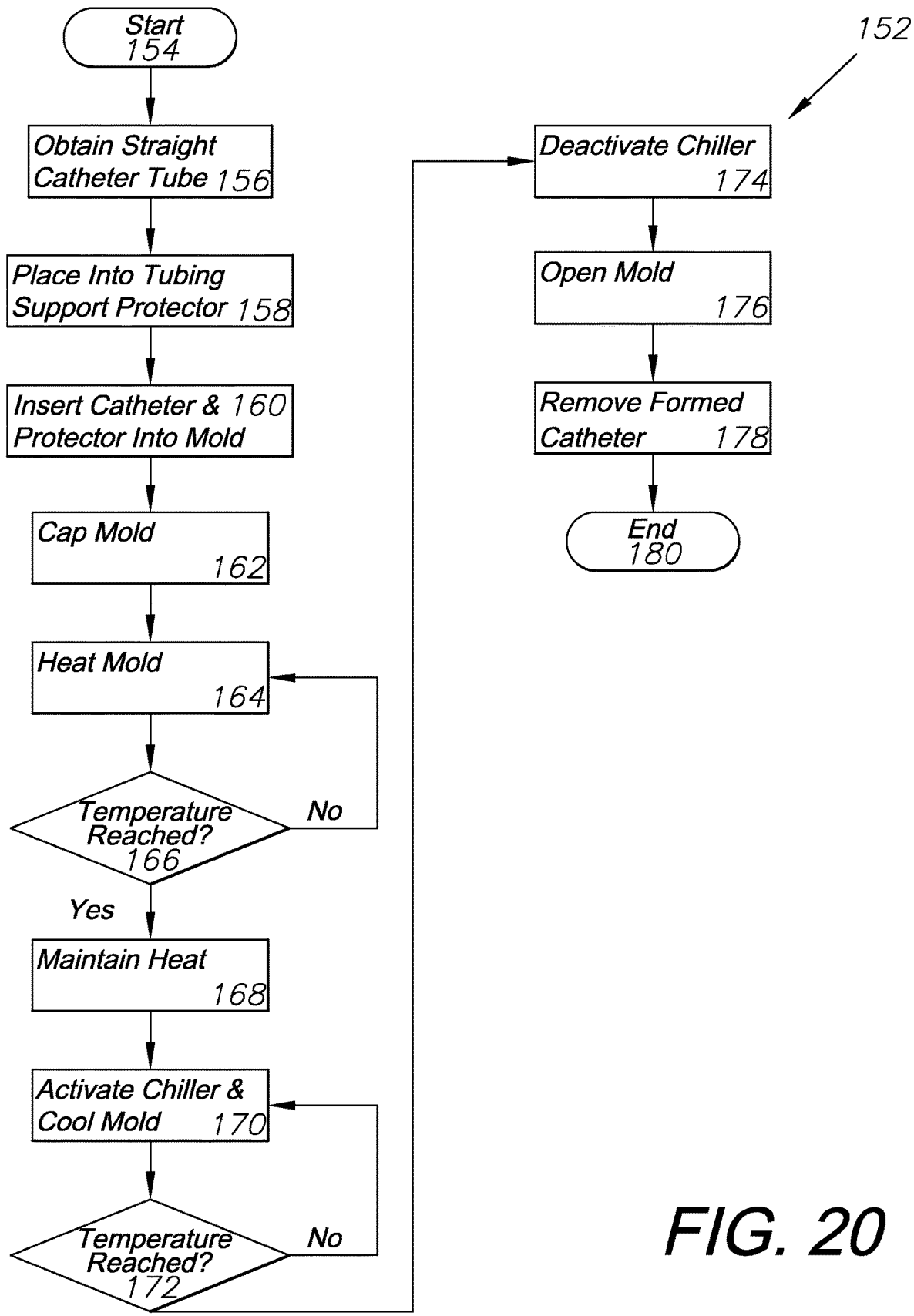
FIG. 20 is a flow chart diagramming the method of manufacturing a preferred embodiment of the present invention.

FIG. 20 shows the steps taken in practicing a method 152 of manufacturing the coil catheter 4 as described above using the manufacturing system 52. The process starts at 154, where a straight catheter tube is obtained at 156. This catheter tube should be cut to size, approximately 8.5" long, and may be outfitted with a tubing support to reduce the risk of tubing kinks during the forming process at 158.

The catheter and protector are then inserted into the mold at 160, using the swan neck form 44 and the halo form 40 of the mold base 34. The mold is capped at 162 and heated at 164 as described above. A check using the temperature gauge 54 is made at 166 to determine if the proper temperature has been reached. If not, heating continues. If so, temperature is maintained at 168 for 15 minutes, after which the chiller is activated at 170 to cool the mold.

A check to determine if the mold has reached its cooled temperature below 80 degrees Fahrenheit at 172. If not, chilling continues. If so, then the chiller is deactivated at 174, the mold is opened at 176, and the formed catheter 4 is removed at 178, ending the process at 180.

The catheter may be manufactured of Carbothane or other materials which provide long safety use and biocompatibility.

It is to be understood that while certain embodiments and/or aspects of the invention have been shown and described, the invention is not limited thereto and encompasses various other embodiments and aspects.

Having thus described the invention, what is claimed as new and desired to be secured by Letters Patent:

1. A method of manufacturing a catheter, the method comprising the steps: placing catheter tube in a straight orientation into a mold base, said mold base comprising a forming block having a swan neck form portion and a halo coil form portion;
   positioning portions of said straight catheter tube within said forming block about said swan neck form portion and said halo coil form portion;
   capping said mold with a mold cap and securing said mold cap to said mold base;
   heating said mold with a heating element;
   cooling said mold with a chiller after ceasing the heating of said mold by deactivating said heating element, wherein the chiller comprises a temperature gauge, wherein the temperature gauge comprises a temperature alarm configured to track chilling, wherein the temperature gauge is further configured to identify a temperature threshold;
   deactivating said chiller as a function of an indicated temperature outside of the identified temperature threshold;
   removing said mold cap; and
   removing said catheter tube, now comprising a catheter body including a proximal end and a distal end, said proximal end comprising a coil having a swan neck element and a right-angle element.

2. The method of claim 1, further comprising the step of placing a tubing support protector into said catheter tube prior to placing said catheter tube into said mold base.

3. The method of claim 1, wherein at least one eyelet is located along a horizontal plane of said catheter tube along said coil, said at least one eyelet configured to facilitate and enhance flow through the catheter.

4. The method of claim 1, further comprising the steps:
   forming a stabilizing elbow via said swan neck element and said right-angle element; wherein said stabilizing elbow terminates into a straight stem culminating in said distal end of said catheter body.

5. The method of claim 4, further comprising the steps:
   providing a single first eyelet located along a horizontal plane of a single coil;
   providing a single second eyelet located along said stabilizing elbow; and
   inserting said catheter body into a subject body such that the catheter body functions as a prosthetic urethral stent while inserted in said subject body with said distal end located above a sphincter.

6. The method of claim 5, further comprising the steps:
   providing a suture-to-tube portion configured to place a suture external to a lumen of said catheter body and external to a pusher, thereby being configured to prevent obstruction and tethering of said catheter body and to allow for bridging said sphincter, positioning the catheter body, and removing the catheter body.

* * * * *